(12) United States Patent
Morris et al.

(10) Patent No.: US 7,758,521 B2
(45) Date of Patent: Jul. 20, 2010

(54) METHODS AND SYSTEMS FOR ACCESSING THE PERICARDIAL SPACE

(75) Inventors: Mary M Morris, Mounds View, MN (US); Kenneth C. Gardeski, Plymouth, MN (US); Michael R. Ujhelyi, Maple Grove, MN (US); Michael E. Leckrone, Collierville, TN (US)

(73) Assignee: Medtronic, Inc., Minneapolis, MN (US)

( * ) Notice: Subject to any disclaimer, the term of this patent is extended or adjusted under 35 U.S.C. 154(b) by 1630 days.

(21) Appl. No.: 11/000,539

(22) Filed: Dec. 1, 2004

(65) Prior Publication Data

US 2005/0165466 A1      Jul. 28, 2005

Related U.S. Application Data

(60) Continuation-in-part of application No. 10/606,908, filed on Jun. 26, 2003, now Pat. No. 7,207,988, which is a division of application No. 09/430,096, filed on Oct. 29, 1999, now Pat. No. 6,613,062.

(51) Int. Cl.
*A61M 25/00* (2006.01)
*A61M 25/01* (2006.01)

(52) U.S. Cl. ............... 600/585; 607/116; 607/119; 604/167.02; 604/167.04; 606/108

(58) Field of Classification Search ............. 607/116, 607/119, 120, 122; 606/41, 108, 167; 604/167.02, 604/167.04, 263
See application file for complete search history.

(56) References Cited

U.S. PATENT DOCUMENTS

| | | | |
|---|---|---|---|
| 4,685,458 A * | 8/1987 | Leckrone ............... 606/7 |
| 4,815,478 A | 3/1989 | Buchbinder et al. |
| 4,946,457 A | 8/1990 | Elliot |
| 4,991,578 A | 2/1991 | Cohen |
| 5,215,527 A * | 6/1993 | Beck et al. ............. 604/164.09 |
| 5,269,326 A | 12/1993 | Verrier |
| 5,330,496 A | 7/1994 | Alferness |
| 5,336,252 A | 8/1994 | Cohen |
| 5,728,148 A | 3/1998 | Bostrom et al. |
| 5,797,870 A | 8/1998 | March et al. |

(Continued)

OTHER PUBLICATIONS

Yamamoto, T., et al. "Minireview Nitric Oxide Donors (44565)" P.S.B.M., vol. 225., pp. 200-206 (2000).

(Continued)

*Primary Examiner*—Roy D Gibson
*Assistant Examiner*—Kaitlyn E Helling

(57) ABSTRACT

Methods and systems for transvenously accessing the pericardial space via the vascular system and atrial wall, particularly through the superior vena cava and right atrial wall, to deliver treatment in the pericardial space are disclosed. A steerable instrument is advanced transvenously into the right atrium of the heart, and a distal segment is deflected into the right atrial appendage. A fixation catheter is advanced employing the steerable instrument to affix a distal fixation mechanism to the atrial wall. A distal segment of an elongated medical device, e.g., a therapeutic catheter or an electrical medical lead, is advanced through the fixation catheter lumen, through the atrial wall, and into the pericardial space. The steerable guide catheter is removed, and the elongated medical device is coupled to an implantable medical device subcutaneously implanted in the thoracic region. The fixation catheter may be left in place.

21 Claims, 12 Drawing Sheets

U.S. PATENT DOCUMENTS

| | | | |
|---|---|---|---|
| 5,827,216 | A | 10/1998 | Igo et al. |
| 5,873,842 | A | 2/1999 | Brennen et al. |
| 5,900,433 | A | 5/1999 | Igo et al. |
| 5,931,810 | A | 8/1999 | Grabek |
| 5,968,010 | A | 10/1999 | Waxman et al. |
| 5,972,013 | A | 10/1999 | Schmidt |
| 6,102,887 | A * | 8/2000 | Altman ................. 604/22 |
| 6,146,338 | A | 11/2000 | Gardeski et al. |
| 6,156,009 | A | 12/2000 | Grabek |
| 6,162,195 | A | 12/2000 | Igo et al. |
| 6,200,303 | B1 | 3/2001 | Verrier et al. |
| 6,206,004 | B1 | 3/2001 | Schmidt et al. |
| 6,231,518 | B1 | 5/2001 | Grabek et al. |
| 6,358,247 | B1 * | 3/2002 | Altman et al. ................. 606/41 |
| 6,592,552 | B1 | 7/2003 | Schmidt |
| 7,103,418 | B2 * | 9/2006 | Laske et al. ................. 607/120 |
| 2004/0116848 | A1 | 6/2004 | Gardeski et al. |

OTHER PUBLICATIONS

Jozkowicz, A., et al. "Genetic augmentations of nitric oxide synthase increases the vascular generation of VEGF", Cardiovascular Research, vol. 51, pp. 773-783 (2001).

Ruel, M. et al. "Inhibition of the Cardiac Angiogenic Response to Surgical FGF-2 Therapy in a Swine Endothelial Dysfunction Model", circulation pp. II-335-II-340.

* cited by examiner

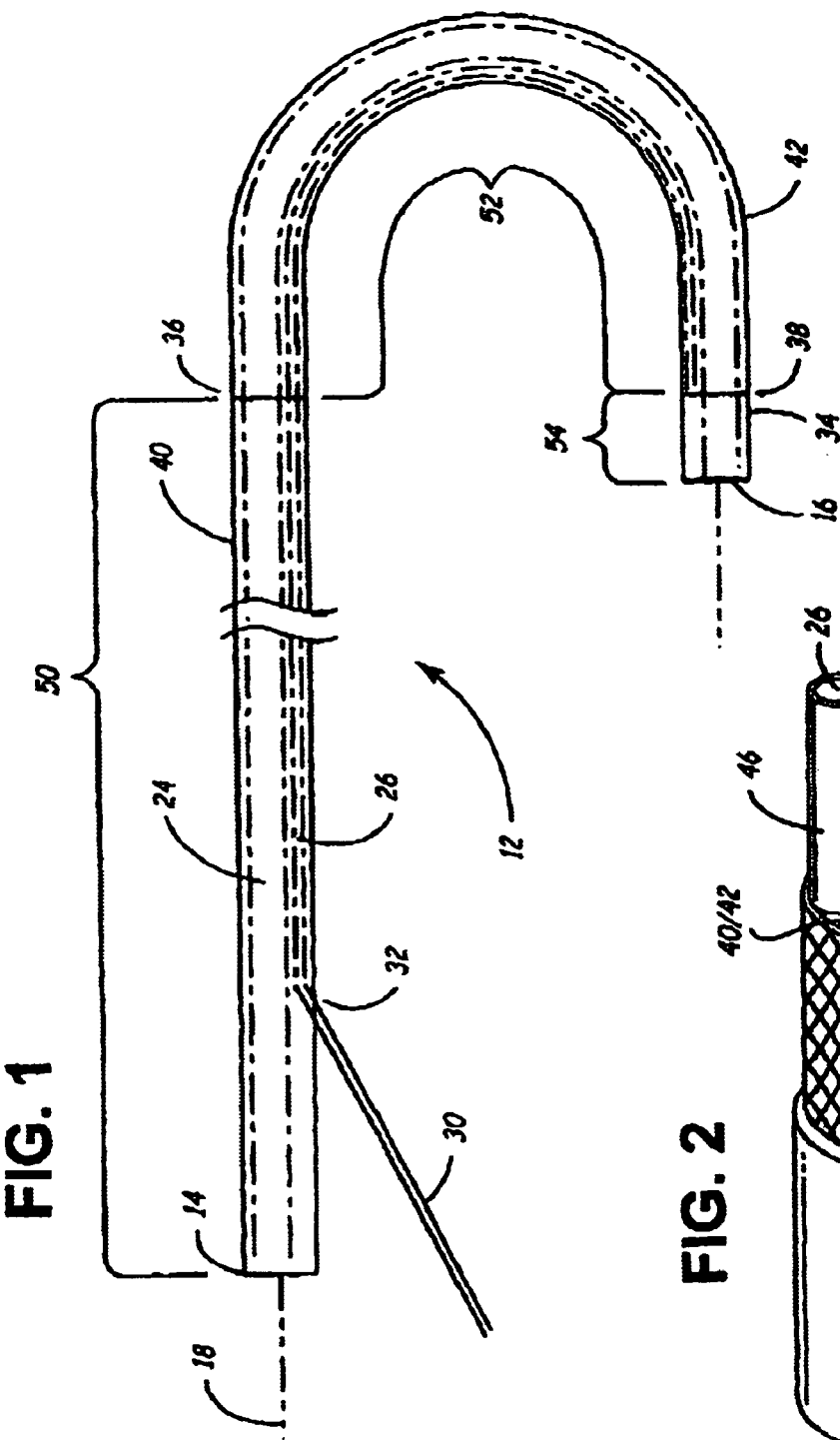

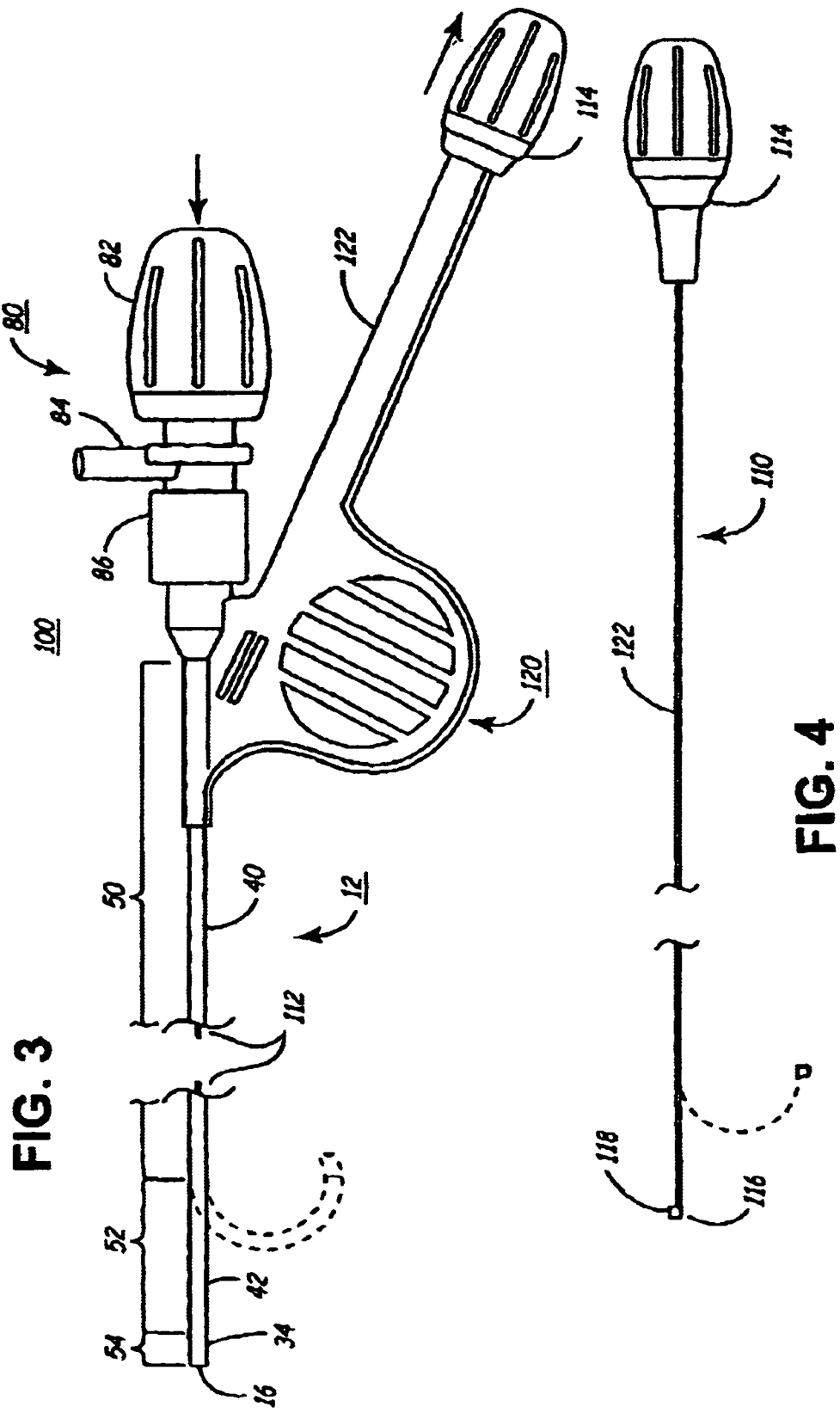

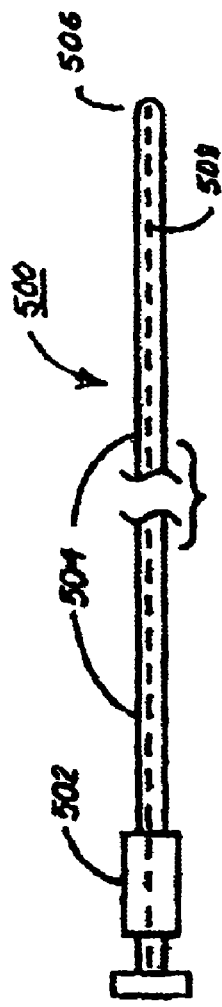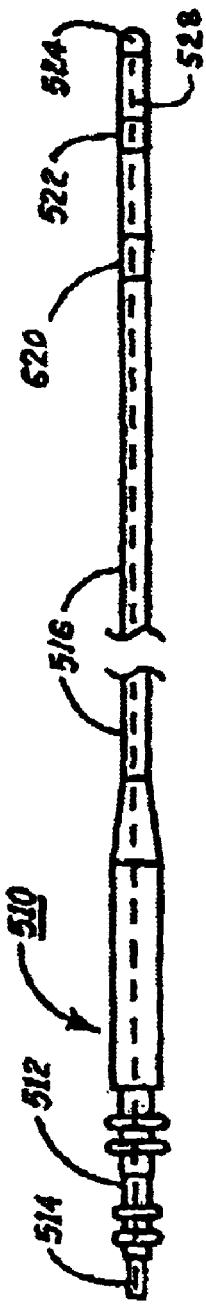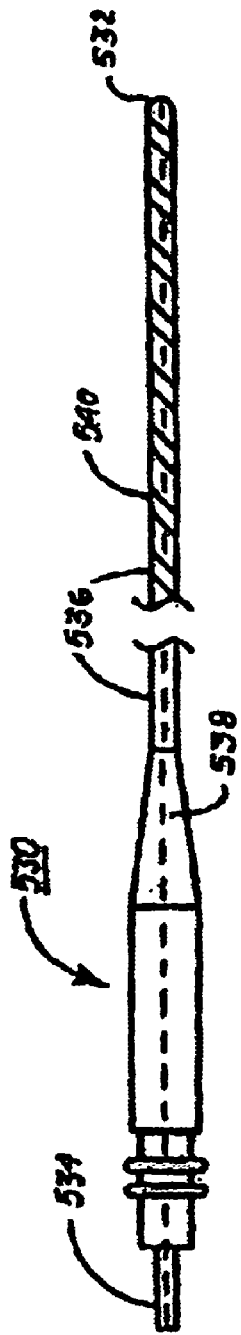

METHODS AND SYSTEMS FOR ACCESSING THE PERICARDIAL SPACE

This application is a continuation-in-part of U.S. patent application Ser. No. 10/606,908, filed Jun. 26, 2003 now U.S. Pat. No. 7,207,988, published as Published Patent Application No. 2004/0087938 A1, which is a division of U.S. patent application Ser. No. 09/430,096, filed Oct. 29, 1999, now U.S. Pat. No. 6,613,062.

FIELD OF THE INVENTION

This invention relates generally to methods and systems for accessing the pericardial space via the vascular system and atrial wall, particularly through the superior vena cava and right atrial wall to deliver treatment in the pericardial space.

BACKGROUND OF THE INVENTION

The human heart wall consists of an inner layer of simple squamous epithelium, referred to as the endocardium, overlying a variably thick heart muscle or myocardium and is enveloped within a multi-layer tissue structure referred to as the pericardium. The innermost layer of the pericardium, referred to as the visceral pericardium or epicardium, clothes the myocardium. The epicardium reflects outward at the origin of the aortic arch to form an outer tissue layer, referred to as the parietal pericardium, which is spaced from and forms an enclosed sac extending around the visceral pericardium of the ventricles and atria. An outermost layer of the pericardium, referred to as the fibrous pericardium, attaches the parietal pericardium to the sternum, the great vessels and the diaphragm so that the heart is confined within the middle mediastinum. Normally, the visceral pericardium and parietal pericardium lie in close contact with each other and are separated only by a thin layer of a serous pericardial fluid that enables friction free movement of the heart within the sac. The space (really more of a potential space) between the visceral and parietal pericardia is referred to as the pericardial space. In common parlance, the visceral pericardium is usually referred to as the epicardium, and epicardium will be used hereafter. Similarly, the parietal pericardium is usually referred to as the pericardium, and pericardium will be used hereafter in reference to parietal pericardium.

Access to the pericardial space is desirable in order to provide a variety of cardiac therapies, including delivery of therapeutic agents (defined herein as including genetic agents, biologic agents, and pharmacologic agents), placement of electrical medical leads for pacing, cardioversion, defibrillation or EGM monitoring, removal of pericardial fluid for diagnostic analysis, or other purposes. A variety of mechanisms have been developed for accessing the pericardial space, ranging from a simple puncture by means of a large bore needle to intricate catheter or cannula based systems provided with sealing and anchoring mechanisms.

Access to the pericardial space may be accomplished from outside the body by making a thoracic or sub-xiphoid incision to access and cut or pierce the pericardial sac. Access to the pericardial space from the exterior of the body, accomplished by passing a cannula or catheter type device through the chest wall and thereafter passing the cannula or catheter or a further instrument through the pericardium into the pericardial space, is disclosed in U.S. Pat. Nos. 5,827,216, 5,900,433, and 6,162,195 issued to Igo, U.S. Pat. No. 5,336,252 issued to Cohen, and U.S. Pat. Nos. 5,972,013, 6,206,004, 6,592,552 by Schmidt, for example. In certain cases the pericardial sac is cut by a cutting instrument as disclosed in U.S. Pat. Nos. 5,931,810, 6,156,009, and 6,231,518 issued to Grabek et al.

Alternatively, an elongated perforating instrument device is introduced from a skin incision by a transvenous or transarterial approach into the right or left heart chambers, respectively, and a cutting or piercing or penetrating mechanism at the distal end of the elongated perforating instrument is operated to penetrate through the atrial or ventricular wall of the right or left heart chamber into the surrounding pericardial space without perforating the pericardial sac. For example, a transvenous catheter provided with a hollow helical needle adapted to rotated and pierce through the wall of a right or left heart chamber to access the pericardial space to deliver pharmacologic agents is disclosed in U.S. Pat. No. 5,797,870 issued to March et al. A transvenous catheter introduced into the right ventricular chamber to provide access through the right ventricular wall to enable passage of an electrical medical lead into the pericardial space is disclosed in, U.S. Pat. No. 4,991,578 issued to Cohen, and U.S. Pat. No. 5,330,496 issued to Alferness, for example.

It is preferable to effect transvenous access into the pericardial space from the right atrial heart chamber through the atrial wall due to the relatively low blood pressure of right atrial blood during systole to lessen the possibility of leakage of blood into the pericardial space. Consequently, it has been proposed to transvenously introduce an elongated electrical medical device through the venous system and either the inferior vena cava or the superior vena cava into the right atrial chamber and perforating through the right atrial wall into the pericardial space. In U.S. Pat. No. 4,946,457 issued to Elliot it is proposed to transvenously introduce an elongated electrical medical lead through the venous system and superior vena cava into the right atrial chamber and perforating through the right atrial wall to advance and dispose the distal electrode of the lead into the pericardial space. It has also been proposed that a preferred site of penetration of catheters or electrical medical leads through the atrial wall into the pericardial space is within the right atrial appendage as disclosed in U.S. Pat. No. 5,269,326 issued to Verrier, U.S. Pat. No. 6,200,303 issued to verrier et al and U.S. Pat. No. 5,968,010 issued to Waxman et al. Transvenous approaches through either of the inferior vena cava or the superior vena cava are disclosed in these patents.

It is customary in the implantation of transvenous cardiac pacing leads and cardioversion/defibrillation leads to access the venous system that drains into the superior vena cava and to lodge and fix a pace/sense or cardioversion/defibrillation electrode within the right ventricle, the right atrium or a cardiac vein accessed through the coronary sinus. The proximal connector ends of such leads are coupled to implantable pulse generators (IPGs) that are implanted subcutaneously in the thoracic region. It is preferable to implant the IPGs in the thoracic region, rather than the groin or abdominal region, because the thoracic region is more stable than the abdominal or groin region during ambulation and other normal body movement and the IPG is less likely to migrate from the subcutaneous implantation site. Consequently, the transvenous access into the right atrium is made through the superior vena cava.

A distal pace/sense electrode of an atrial pacing lead is typically lodged into the atrial appendage and various active and passive fixation mechanisms are employed to hold the electrode in place. Atrial pacing leads have been designed in a variety of ways to overcome the inherent difficulty of routing the distal end of an atrial lead or any other elongated medical device through the superior vena cava into the right atrial heart chamber and then into the atrial appendage. However, care is taken in the design of such leads and delivery mechanisms and techniques to avoid perforating the atrial wall.

It is proposed in the above-referenced '326 patent to alternatively route a pacing lead or cardioversion/defibrillation lead through a perforation of the atrial wall in the atrial appendage to lodge a pace/sense electrode and/or cardioversion/defibrillation electrode within the pericardial space and to subcutaneously implant an IPG or implantable monitor or drug dispenser in the thoracic region. The suggested routing of the electrical medical lead or catheter is through the thoracic venous system, through the superior vena cava, and through the atrial wall of the atrial appendage into the pericardial space.

It is a relatively simple matter to route a perforating instrument through the venous system draining into the right atrium through the inferior vena cava since the instrument body is relatively straight within the right atrium and axial force can be applied to perforate the atrial wall while observing the advancement under fluoroscopy. It is not a simple matter to advance the distal end perforating mechanisms of the perforating instruments disclosed in the above-identified patents through the superior vena cava into the right atrial heart chamber and then into the atrial appendage. The physiology and shape of the atrial appendage requires that the direction of advancement of the distal end be reversed or abruptly changed after it is disposed in the right atrial heart chamber. Moreover, the atrial wall in the atrial appendage tends to yield somewhat if blunt force is applied against its endocardial surface. Consequently, the precise application of perforating force and advancement of the distal end perforating element must be carefully controlled, which is difficult to manage through the bend in the instrument body.

It would therefore be desirable to provide a method and system for accessing the atrial appendage via the superior vena cava and applying force through an elongated perforating instrument sufficient to safely penetrate through or perforate the atrial wall without penetrating or perforating the pericardial sac enclosing the pericardial space.

In addition, after the perforation is made, the transvenous advancement of an electrical medical lead or therapeutic catheter through the perforation made in the atrial wall via the superior vena cava can be difficult to accomplish. It would be desirable that such a system and method facilitate that advancement.

It would also be particularly desirable to facilitate access to the pericardial space to enable chronic delivery of pharmacologic agents to the heart as suggested in the above-referenced '326, '303, and '010 patents. In particular it is noted that the pericardial fluid provides an excellent medium for delivery of pharmacologic agents to the cardiac muscles and coronary vessels without distribution to other organs. Among the clinically significant pharmacologic agents (i.e., drugs) which could advantageously be delivered to the heart via the pericardial fluid are those which improve cardiac contractility (e.g., digitalis drugs, adrenergic agonists, etc.), suppress arrhythmias (e.g., class I, II, III, and IV agents and specialized drugs such as amiodarone, which is particularly potent but has severe systemic side effects), dilate coronary arteries (e.g., nitroglycerin, calcium channel blockers, etc.), and lyse clots in the coronary circulation (e.g., thrombolytic agents such as streptokinase or tissue-type plasminogen activator (TPA)).

Examples of other pharmacologic agents which may be administered into the pericardial space include: agents to protect the heart pharmacologically from the toxic effects of drugs administered to the body generally for other diseases, such as cancer; antibiotics, steroidal and non-steroidal medications for the treatment of certain pericardial diseases; and growth factors to promote angiogenesis or neovascularization of the heart.

The delivery of further pharmacologic agents into the pericardial space is disclosed in the above-referenced '433 patent, wherein cardio-active or cardio-vascular active drugs are selected from vasodilator, antiplatelet, anticoagulant, thrombolytic, anti-inflammatory, antiarrhythmic, inotropic, antimitotic, angiogenic, antiatherogenic and gene therapy bioactive agents. The approaches to the pericardial space include those disclosed in the above-referenced '326 patent or transthoracically, e.g., under the xiphoid process, i.e., by a sub-xiphoid surgical approach.

In particular, it is proposed in the '433 patent to deliver such pharmacologic agents into the pericardial space to treat or to prevent vascular thrombosis and angioplasty restenosis, particularly coronary vascular thrombosis and angioplasty restenosis, thereby to decrease incidence of vessel rethrombosis, unstable angina, myocardial infarction and sudden death. It is proposed to deliver a congener of an endothelium-derived bioactive agent, more particularly a nitrovasodilator, representatively the nitric oxide donor agent sodium nitroprusside, to the pericardial space at a therapeutically effective dosage rate to abolish cyclic coronary flow reductions (CFR's) while reducing or avoiding systemic effects such as suppression of platelet function and bleeding. Particular congeners of an endothelium-derived bioactive agent include prostacyclin, prostaglandin $E_1$, and a nitrovasodilator agent. Nitrovasodilater agents include nitric oxide (NOX) and NOX donor agents, including L-arginine, sodium nitroprusside and nitroglycycerine. The so-administered nitrovasodilators are effective to provide one or more of the therapeutic effects of promotion of vasodilation, inhibition of vessel spasm, inhibition of platelet aggregation, inhibition of vessel thrombosis, and inhibition of platelet growth factor release, at the treatment site, without inducing systemic hypotension or anticoagulation.

The above-referenced '433 patent also discloses intrapericardial injection of drugs for the treatment of malignant or loculated pericardial effusions in man. Drugs that have been injected into the pericardial space include antibiotic, antineoplastic, radioactive and fibrinolytic agents. This method of site-specific drug delivery has been shown to be effective in attaining higher, longer-lasting drug levels in the pericardial fluid with lower plasma concentrations and less systemic toxicity.

It is therefore desirable to provide a system and method for chronically accessing the pericardial space to deliver such therapeutic agents to treat cardiac disorders or to prevent or ameliorate a cardiac insult.

BRIEF SUMMARY OF THE INVENTION

Accordingly, the present invention provides systems and methods that access a desired location through a tissue wall within a patient's body, e.g., the pericardial space through the right atrial wall in the atrial appendage via the venous system draining through the superior vena cava into the right atrium to enable chronic implantation of a distal segment of a therapeutic catheter, e.g., a drug delivery catheter coupled to a drug pump, or an electrical medical lead coupled to an IPG or implantable heart monitor (IHM), in the pericardial space.

In a preferred embodiment of the present invention, the system comprises an elongated steering instrument, an elongated fixation catheter, and an elongated tissue penetration instrument. The elongated tissue penetration element may be separate from or may be incorporated into an elongated medical device comprising one of an electrical medical lead and/or a therapeutic catheter.

The electrical medical lead or therapeutic catheter and the elongated fixation catheter may advantageously be left in place during chronic implantation after a distal segment of the therapeutic catheter or electrical medical lead is lodged in the desired location, and the proximal end of the therapeutic catheter is coupled to an implantable infusion pump (IIP) or the proximal end of the electrical medical lead is coupled to an IPG or IHM.

One form of an elongated steering instrument comprise a steerable guide catheter of the type having a guide catheter delivery lumen terminating in a delivery lumen exit port at a guide catheter distal end, a deflectable distal segment, and a deflector operable from the guide catheter proximal end to steer the guide catheter distal end to the tissue wall. The elongated fixation catheter has a fixation catheter lumen extending between proximal and distal fixation catheter lumen openings, a penetrable seal closing the fixation catheter lumen, and a distal tissue fixation mechanism, the fixation catheter sized to be extend through said guide catheter delivery lumen to dispose said distal fixation mechanism and distal fixation catheter lumen opening proximate the tissue wall. The elongated fixation catheter is adapted to be manipulated to extend the distal fixation mechanism away from the distal guide catheter delivery lumen opening into the atrial wall to engage and stabilize the atrial wall. The elongated penetration instrument has a tissue-penetrating element sized and adapted to be passed through the fixation catheter lumen, through the penetrable seal and through the tissue wall into the desired location.

Alternatively, the elongated steering instrument comprises a steerable stylet or guidewire having an outer tubular member and an inner member wherein a distal segment may be selectively deflected to induce a like deflection in the fixation catheter.

The distal fixation mechanism is preferably a fixation helix extending distally from the penetrable seal and adapted to be rotated and screwed into tissue wall.

The tissue wall is preferably the right atrial wall within the atrial appendage that is accessed by advancing the steerable guide catheter through a venous pathway and the superior vena cava into the right atrial chamber and deflecting the deflectable distal segment of the guide catheter body to dispose the delivery lumen exit port against the right atrial wall. The desired location is preferably the pericardial space accessed by a perforation through the right atrial wall.

The methods and systems of the present invention would be best used with an implantable drug pump coupled to a therapeutic agent delivery therapeutic catheter extending through the fixation catheter lumen, through the penetrable seal and through the tissue wall into the desired location, preferably through the right atrial wall into the pericardial space. Similarly, the methods and systems of the present invention would be best used with an IPG or an IHM coupled to an electrical medical lead extending through the fixation catheter lumen, through the penetrable seal and through the tissue wall into the desired location, preferably through the right atrial wall into the pericardial space.

Advantageously, the fixation catheter may be removed or left in place to maintain a seal of the right atrial wall and to protect or reinforce the electrical medical lead or therapeutic catheter extending through the venous pathway to the perforation of the right atrial wall.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 1 is a schematic illustration of a bilumen guide catheter body;

FIG. 2 is a perspective sectional view of the bilumen guide catheter body of FIG. 1;

FIG. 3 is plan view of a guide catheter incorporating the guide catheter body of FIG. 1 with a guide catheter hub and deflection wire;

FIG. 4 is a plan view of the deflection wire incorporated into the guide catheter of FIG. 3;

FIG. 8 is a plan view of a therapeutic catheter, e.g., a drug infusion or drainage or fluid sampling catheter, adapted to be advanced through the fixation catheter lumen, the penetrable seal, and the right atrial wall into the pericardial space in FIGS. 6 and 7;

FIGS. 9 and 10 are plan views of electrical medical leads adapted to be advanced through the fixation catheter lumen, the penetrable seal, and the right atrial wall into the pericardial space in FIGS. 6 and 7 to dispose one or more of a pace/sense electrode, a cardioversion/defibrillation electrode, and a sensor in the pericardial space at a selected site of the left atrium and/or left ventricle;

DETAILED DESCRIPTION OF THE PREFERRED EMBODIMENTS OF THE INVENTION

Figure 5:
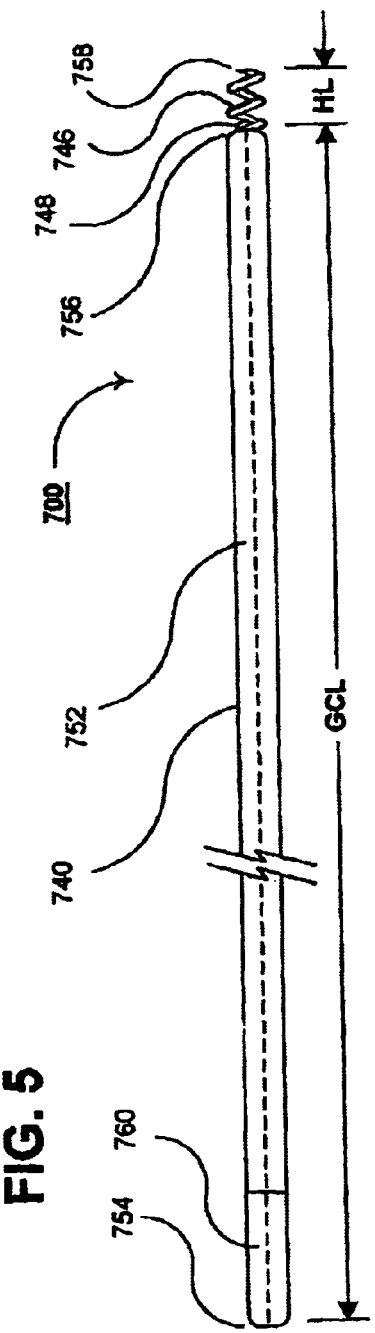
FIG. 5 is a plan view of a fixation catheter having a fixation catheter lumen closed by a penetrable seal at the fixation catheter body distal end and a distally extending fixation helix.

In the following detailed description, references are made to illustrative embodiments of methods and apparatus for carrying out the invention. It is understood that other embodiments can be utilized without departing from the scope of the invention.

The present invention can be implemented employing steerable guide catheters having a single lumen or multiple lumens extending the length of the therapeutic catheter body. For convenience, the illustrated preferred embodiments depict steerable therapeutic catheters having at least one delivery lumen and a deflection lumen that can receive a deflection mechanism to induce bends and curves in at least an intermediate segment of the therapeutic catheter body.

For example, one possible form of steerable guide catheter is disclosed in commonly assigned Patent Application Publication US 2004/0116848 published Jun. 17, 2004 and depicted in FIGS. 1-4. A bilumen therapeutic catheter body 12 is depicted in FIGS. 1 and 2, which forms part of a steerable guide catheter 10 depicted in FIG. 3, with a bend induced in the intermediate segment 52 thereof. The elongated therapeutic catheter body 12 has a therapeutic catheter axis 18 and extends from a therapeutic catheter body proximal end 14, which is adapted to be coupled with and separated from the therapeutic catheter hub 80 shown in FIG. 3, to a therapeutic catheter body distal end 16. A delivery lumen 24 extends through the therapeutic catheter body 12 from a delivery lumen proximal end opening at the therapeutic catheter body proximal end 14 to a delivery lumen distal end opening at the therapeutic catheter body distal end 16. A deflection lumen 26 extends alongside the delivery lumen 24 through the therapeutic catheter body 12 from a deflection lumen proximal end opening 32 through sheath 34 to either a deflection lumen closed distal end proximal to the therapeutic catheter body distal end 16 or a deflection lumen distal end opening at the therapeutic catheter body distal end 16, depending upon the type of steerable therapeutic catheter formed with the steerable therapeutic catheter body 12.

Generally speaking, the therapeutic catheter body 12 includes a number of segments, e.g., segments 50, 52 and 54, along its length formed of different materials and structural components to provide different handling characteristics. The segments 50 and 52 are formed of respective outer sheath segments 40 and 42 of materials that contribute to making the most proximal segment 50 relatively stiff to impart column strength and torqueability and to making intermediate segment 52 more flexible and bendable upon manipulation of the deflection mechanism. The distal segment 54 incorporates a soft sheath 34 that is intended to be atraumatic at therapeutic catheter body distal end 16 to avoid injury to tissue. Intermediate segment 52 is axially joined to proximal segment 50 at junction 36, and the intermediate segment 52 is joined to distal segment 54 at junction 38. The present invention improves the flexibility of the bendable intermediate segment 52 and the characteristics of the atraumatic distal segment 54 and offers further advantages in fabrication and handling characteristics.

The deflection lumen 26 is adapted to receive a deflection mechanism 30 extended through in the outer sheath side opening 32 operable to selectively impart a bend in the intermediate segment 52 of the therapeutic catheter body 12. The deflection mechanism 30 shown schematically in FIG. 1 comprises one of a permanently inserted and distally attached deflection wire, a removable stylet, a removable guide wire or conductors for applying current to and resistively heating a shape memory alloy strip inserted into the intermediate segment 52. The removable stylet can be a steerable stylet of the types described in commonly assigned U.S. Pat. Nos. 5,873,842 and 6,146,338, for example.

Referring to FIG. 2, the therapeutic catheter body 12 is formed of a proximal outer sheath segment 40 and an intermediate outer sheath segment 42 encasing a tubular wire braid 28, a delivery lumen liner 44 defining delivery lumen 24, and a deflection lumen liner 46 defining the deflection lumen 26. The delivery and deflection lumen liners 44 and 46 may have a substantially uniform cross-sectional area along the lengths thereof or may vary along the lengths thereof. It is desirable for the therapeutic catheter body 12 to be constructed to assure that the delivery and deflection lumens 24 and 26 maintain their cross-sectional shape and to provide the desired flexibility, pushability, torqueability and low profile of the therapeutic catheter body 12 required for its intended use in a steerable therapeutic catheter. It is further desirable that the inner surfaces of the lumen liners 44 and 46 are lubricious to enable free passage or movement of devices therethrough. It is also desirable that the lumen liners 44 and 46 resist rupture or penetration. The lumen diameter and wall thickness of the deflection lumen liner 46 and its specific properties may depend in part upon the diameter and type of deflection mechanism 30 intended to be inserted into the deflection lumen 26 and the requisite clearance to assure smooth movement of a movable deflection mechanism. The tubular wire braid 28 may be of a variety of different materials and configurations designed to impart the desired stiffness to the therapeutic catheter shaft section and in particular ensure that the cross-sectional shape of the delivery and deflection lumen liners 44 and 46 to remain substantially undistorted as the therapeutic catheter body 12 undergoes high flexure encountered traversing sharp bends in the vascular pathway. Exemplary materials, material characteristics, and methods of fabrication of the components of the therapeutic catheter body 12 are described in detail in the above referenced Patent Application Publication 2004/0116848.

The steerable guide catheter 100 illustrated in FIG. 3 comprises the therapeutic catheter body 12 modified at the therapeutic catheter body distal end 16 and attached at the therapeutic catheter body proximal end 14 to a universal hub 120. Universal hub 120 is formed of hub body 60, modified by the depicted elongated side port extension 122 and incorporating a hemostasis valve. Preferably, the universal handle 120 is separable from the therapeutic catheter body proximal end 14 or the therapeutic catheter body 12 and the universal handle 120 are splittable to enable removal from any elongated medical device delivered through the guide catheter delivery lumen.

The deflection mechanism 30 of the steerable therapeutic catheter 100 illustrated in FIG. 3 preferably comprises a deflection wire 110 that is also depicted in FIG. 4. The deflection wire 110 is inserted through the hub deflection lumen 64 and the therapeutic catheter body deflection lumen 26 that collectively comprise a deflection wire lumen and is affixed at the deflection wire lumen distal end to the therapeutic catheter body 12. The therapeutic catheter body distal segment 54 only comprises a distal segment of the delivery lumen liner 44 and the distal outer sheath 34 (shown in broken lines to illustrate interior components). The deflection lumen liner 46 is truncated proximal to the therapeutic catheter body distal end 16. The distal outer sheath 34 is reflow molded in the distal segment 54 to encase the depicted components to either provide the therapeutic catheter body distal end 16 having the same diameter as the therapeutic catheter body 12 along its length as depicted or having a taper to a reduced diameter surrounding the distal end of the delivery lumen liner 44.

The deflection wire 110 comprises a length of stainless steel wire 112 extending from a proximal knob 114 coupled to the proximal end of stainless steel wire 112 to a ring 118 welded to the deflection wire distal end 116. The wire 112 can have a diameter of about 0.008 inches tapered down to 0.006 inches. In this illustrated fabrication of steerable therapeutic catheter 100, the stainless steel wire 112 extends from the distal point of attachment proximally through the deflection wire lumen 26 extending through the intermediate segment 52 and the non-deflectable proximal segment 50 of the therapeutic catheter body 12 and then through the hub deflection wire lumen 64 within side branch or port 122. The deflection wire knob 114 can be pulled away from the side branch or port to induce the bend in the intermediate outer sheath segment 42 depicted in broken lines.

The guide catheter body 12 can be between about 50 cm and 300 cm in length, but is typically and more preferably between about 65 cm and 80 cm in length. The guide catheter body 12 is preferably circular or slightly oval or triangular in cross-section and having a maximal outer diameter in the range of 7 French (2.3 mm) to 14 French (4.7 mm). Typically, proximal segment 50 constitutes about 70-90% of the total length of therapeutic catheter body 12, and relatively more flexible intermediate segment 52 and distal segment 54 constitute the remaining 10%-30% of the length of therapeutic catheter body 12. The delivery lumen diameter is preferably about 0.120 inches (3.0 mm), and the deflection lumen diameter is preferably about 0.020 inches (0.5 mm).

An exemplary elongated fixation catheter 700 is depicted in FIG. 5 that comprises a fixation catheter body 740 that extends from a fixation catheter body proximal end 754 to a fixation catheter distal end 756. The elongated fixation catheter 700 has a fixation catheter lumen 752 extending between proximal and distal fixation catheter lumen openings at the respective fixation catheter proximal and distal ends 754 and 756. A distal tissue fixation mechanism, in this instance a fixation helix 746 is mounted to extend distally from the fixation catheter distal end 756, terminating in a sharp tissue penetrating helix point 758.

Figure 6:
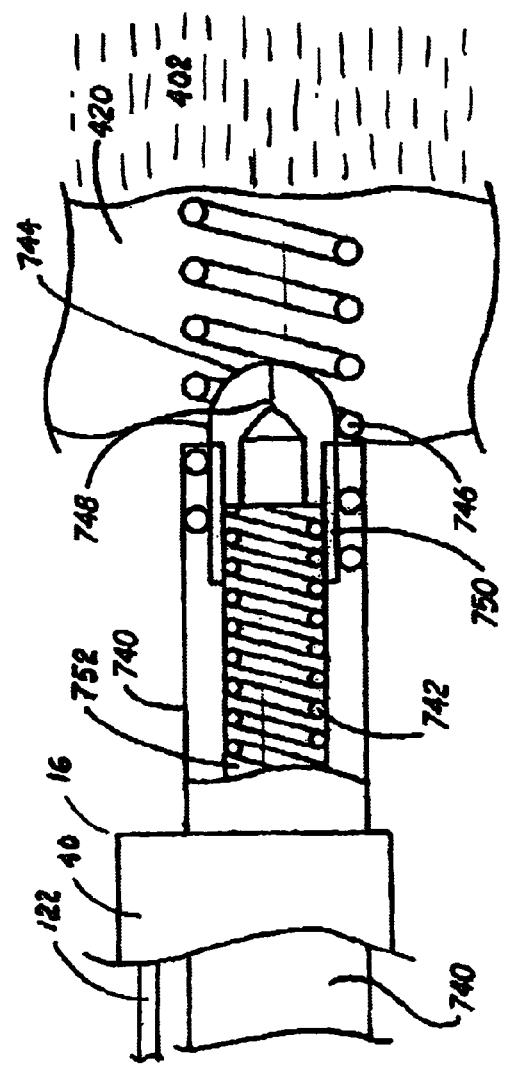
FIG. 6 is a partial section view of a distal segment of the fixation catheter of FIG. 5 extending from the delivery lumen exit port of the steerable guide catheter of FIG. 3 with the fixation helix screwed into a tissue wall, particularly the right atrial wall.
Figure 7:
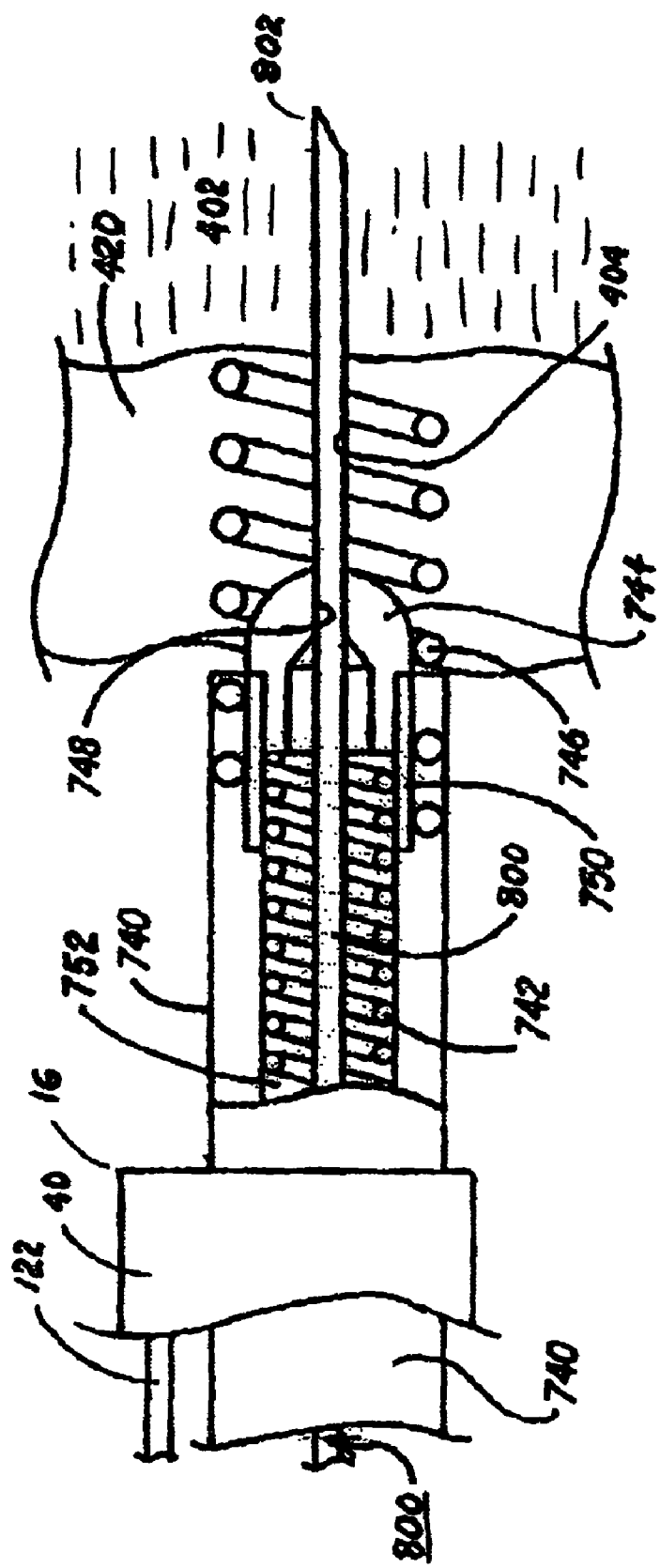
FIG. 7 is a partial section view of the distal segments of the fixation catheter and steerable guide catheter as in FIG. 6 with an elongated tissue penetration instrument extending through the fixation catheter lumen, the penetrable seal, and the right atrial wall into the pericardial space.

The fixation catheter length FCL exceeds the length of the steerable guide catheter 100. The diameter of the fixation catheter 700 is preferably uniform through length FCL and the helix length HL and fits into the delivery lumen 24 of steerable guide catheter 100 as the steerable guide catheter distal end is advanced to a tissue wall, particularly the right atrial wall 420 in the atrial appendage as shown in FIGS. 6 and 7.

In the preferred use of the embodiments of the invention, the steerable therapeutic catheter 100 is advanced through a tortuous venous pathway through the superior vena cava and into the right atrium, and the guide catheter body distal end 16 is deflected into the atrial appendage. The distal fixation helix 746 and a distal segment or segment of the fixation catheter body 740 are advanced from the guide catheter delivery lumen 24 to extend from the guide catheter distal end 16 and screwed into the tissue wall, particularly the right atrial wall 420.

To accomplish this, the fixation helix 746 is adapted to be advanced from the guide catheter delivery lumen exit port so that helix point 758 penetrates the endocardium. The fixation catheter body 740 extends proximally from the guide catheter hub 80 and is adapted to be grasped near proximal end 754 and rotated to screw the distal fixation helix 746 into the right atrial wall 420 as shown in FIG. 6. The number of helix turns and the helix length HL are selected to provide adequate fixation to the right atrial wall 420 without perforating through it when the helix 746 is screwed into the right atrial wall 420.

The distal fixation helix 746 is typically formed of an electrically conductive platinum-iridium alloy that is typically employed for chronic fixation of electrical medical leads to cardiac tissue. Therefore, fixation catheter 700 can optionally be formed to be used as a pacing lead to deliver pacing pulses and sense atrial electrical activity through the fixation helix 746. In this variation, a coiled wire conductor 742 shown in FIG. 6 extends from a distal crimp sleeve 750 attached to the fixation helix 746 proximally within the fixation catheter lumen 752 to a connector element 760 adapted to inserted into a connector bore of an IPG or monitor in a manner well known in the art.

As shown in FIGS. 6 and 7, the delivery lumen exit port at the fixation catheter distal end 756 is closed by a molded polymer (e.g., silicone rubber) seal 744. having a pre-formed slit 748. Seal 744 is flexible and penetrable by an elongated tissue-penetrating instrument 800 that passes through slit 748 as depicted in FIG. 7. The elongated tissue-penetrating instrument 800 has a sharp penetrating tip or element 802 that can be advanced through the penetrable seat 744 (by widening lit 748), and then advanced axially, within the turns of the fixation helix 746, through the right atrial wall 420, and into the pericardial space 402. The elongated tissue penetrating instrument 800 is advanced through the fixation catheter lumen 752 after the fixation helix is 746 is screwed into the right atrial wall 420.

The elongated penetration instrument 800 may simply function to create a perforation 404 through right atrial wall 420 axially aligned with the fixation catheter lumen 752 whereupon the elongated penetration instrument 800 is withdrawn from the fixation catheter lumen 752. In this case, the penetration instrument may comprise a stylet or a guidewire having a relatively stiff sharp distal tip penetrating element 802 that passes through the penetrable seal 748 and penetrates or perforates the right atrial wall 420 as it is advanced and is then withdrawn. In this instance, one of a therapeutic catheter, e.g., a gene delivery catheter or a drug delivery catheter, a drainage or fluid sampling catheter, and an electrical medical lead bearing one or more of a sense electrode, a stimulation electrode, e.g., a pace/sense electrode or cardioversion/defibrillation electrode, and a physiologic sensor, e.g. a pressure sensor, a temperature sensor or a cardiac motion or acceleration sensor, may be advanced through fixation catheter lumen 752, through penetrable seal 744, through the perforation 404 and to a desired site or location in the pericardial space 402 adjacent the left atrium or left ventricle.

If penetration instrument 800 is a guidewire, the therapeutic catheter may be advanced over the guidewire through fixation catheter lumen 752, through penetrable seal 748, through the perforation 404 and to a desired site or location in the pericardial space 402 adjacent the left atrium or left ventricle, and the guidewire may then be withdrawn. An electrical medical lead having a through lumen may be advanced over the guidewire through fixation catheter lumen 752, through penetrable seal 744, through the perforation 404 and to a desired site or location in the pericardial space 402 adjacent the left atrium or left ventricle, and the guidewire may then be withdrawn.

Alternatively, the elongated penetration instrument 800 may comprise one of a therapeutic catheter, e.g., a gene delivery catheter or a drug delivery catheter, a drainage or fluid sampling catheter, and an electrical medical lead bearing one or more of a sense electrode, a stimulation electrode, e.g., a pace/sense electrode or cardioversion/defibrillation electrode, and a physiologic sensor, e.g. a pressure sensor, a temperature sensor or a cardiac motion or acceleration sensor, all adapted to be advanced through fixation catheter lumen 752, through penetrable seal 744, through the perforation 404 and to a desired site or location in the pericardial space 402 adjacent the left atrium or left ventricle.

FIGS. 8-10 illustrate various types of elongated medical devices that may be introduced through the fixation catheter lumen 752 into the pericardial space 402 as illustrated in FIG. 7 for temporary or chronic use. In each case, the elongated medical device includes a device body that is sized to fit into the fixation catheter lumen and pass through the penetrable seal 744 and may include a through lumen that enables advancement over a guidewire that may be employed as the tissue penetrating instrument 800.

A therapeutic catheter 500 is illustrated in FIG. 8 for delivery of drugs or withdrawal of fluids from the pericardial space 402. The therapeutic catheter 500 may be employed as a therapeutic catheter, e.g., a gene delivery catheter or a drug delivery catheter or a drainage or fluid sampling catheter. The therapeutic catheter 500 comprises an elongated therapeutic catheter body 504 extending between a proximal fluid connector 502 and a therapeutic catheter body distal end 506. A fluid transmitting lumen 508 extends from a proximal lumen end opening at the fluid connector 502 and one or more delivery lumen exit ports at or near the therapeutic catheter body distal end 506. Fluid transmitting lumen 508 may function as a through lumen for over the wire advancement of the therapeutic catheter body 504 over a guidewire if a delivery lumen exit port is axially aligned with fluid transmitting lumen.

The fluid connector 502 is shaped and adapted to be coupled to an implantable drug dispenser for chronic dispensation of drugs or agents from a reservoir of an IIP into the pericardial space 402. Alternatively, the fluid connector can be located outside the patient's body and attached to an external drug dispenser temporary delivery of drugs or therapeutic agents or fluid evacuation device for temporarily sampling or draining pericardial fluid from the pericardial space 402.

An electrical medical lead 510 is depicted in FIG. 9 for transmission of electrical signals from the heart or a physiologic sensor or delivery of electrical stimulating pulses, e.g., pacing pulses, to one or more of the left atrium and left ventricle. The electrical medical lead 510 may be adapted for chronic implantation to be coupled to a subcutaneously implanted IPG or IHM or may be extended through the patient's skin to an external pulse generator or monitor for temporary use. The electrical medical lead 510 bears one or more of a sense electrode and a stimulation electrode, e.g., one or more pace/sense electrode and/or a physiologic sensor, e.g. a pressure sensor, a temperature sensor or a cardiac motion or acceleration sensor.

For example, the electrical medical lead 510 is formed of an elongated lead body 516 extending between a proximal lead connector comprising a connector ring 512 and a connector pin 514 and a distal tip pace/sense electrode 524. The proximal lead connector is shaped and adapted to be coupled to a subcutaneously implanted IPG or monitor or can be located outside the patient's body and attached to an external pulse generator or monitor for temporarily pacing or monitoring the heart from the pericardial space 402. A proximal ring pace/sense electrode 522 and a physiologic sensor 520, e.g., a pressure sensor, are disposed along the elongated lead body 516 proximal to the distal tip pace/sense electrode 524. Lead conductors extend within lead body between the proximal connector ring 512 and pin 514 and the pace/sense electrodes 522 and 524 and the physiologic sensor 520. The physiologic sensor 520 and the pace/sense electrode 522 may be combined so that electrical medical lead 510 functions in the manner of the combined pacing and pressure sensing lead disclosed in commonly assigned U.S. Pat. No. 5,564,434. A lead lumen 528 extends from a proximal lumen end opening axially through connector pin 514 through the length of the lead body 516 and either terminates at extends axially through tip pace/sense electrode 524 to function as a stylet lumen or a through lumen for over the wire advancement of the lead body 516 over a guidewire.

A further electrical medical lead 530 comprising a cardioversion/defibrillation lead is depicted in FIG. 10 that would typically be employed with at least one more cardioversion/defibrillation lead adapted to be disposed about the heart and coupled to a cardioversion/defibrillation IPG. The electrical medical lead 530 and the other cardioversion/defibrillation lead would typically also include pace/sense electrodes and connector elements as described above with respect to electrical medical lead 510 to enable sensing and processing of heart signals to trigger delivery of cardioversion/defibrillation shocks or pacing therapies as necessary.

The electrical medical lead 530 is formed of an elongated lead body 536 extending between a proximal lead connector comprising a connector pin 534 and a lead body distal tip 532. The proximal lead connector is shaped and adapted to be coupled to a subcutaneously implanted cardioversion/defibrillation IPG. An elongated, relatively large surface area cardioversion/defibrillation electrode 540 extends along a distal segment of the lead body 536 that would be disposed within the pericardial space 402 alongside the left ventricle to deliver cardioversion/defibrillation shocks through the mass of the left ventricle. A lead conductor extends within lead body 536 between the proximal connector pin 534 and the cardioversion/defibrillation electrode 540. A lead lumen 538 extends from a proximal lumen end opening axially through connector pin 534 through the length of the lead body 536 and either terminates at extends axially through distal tip 532 to function as a stylet lumen or a through lumen for over the wire advancement of the lead body 536 over a guidewire.

The heart 400 and the surrounding pericardial sac 406 depicted in FIGS. 11-14 are cut away in part to expose the epicardium and the right heart chambers of the right atrium (RA) and the right ventricle (RV), which are separated by the tricuspid valve). Venous blood drains into the RA through the superior vena cava (SVC) and the inferior vena cava (not shown). The RA appendage 408 extends somewhat laterally of the axis of the RA between the SVC and tricuspid valve.

Figure 11:
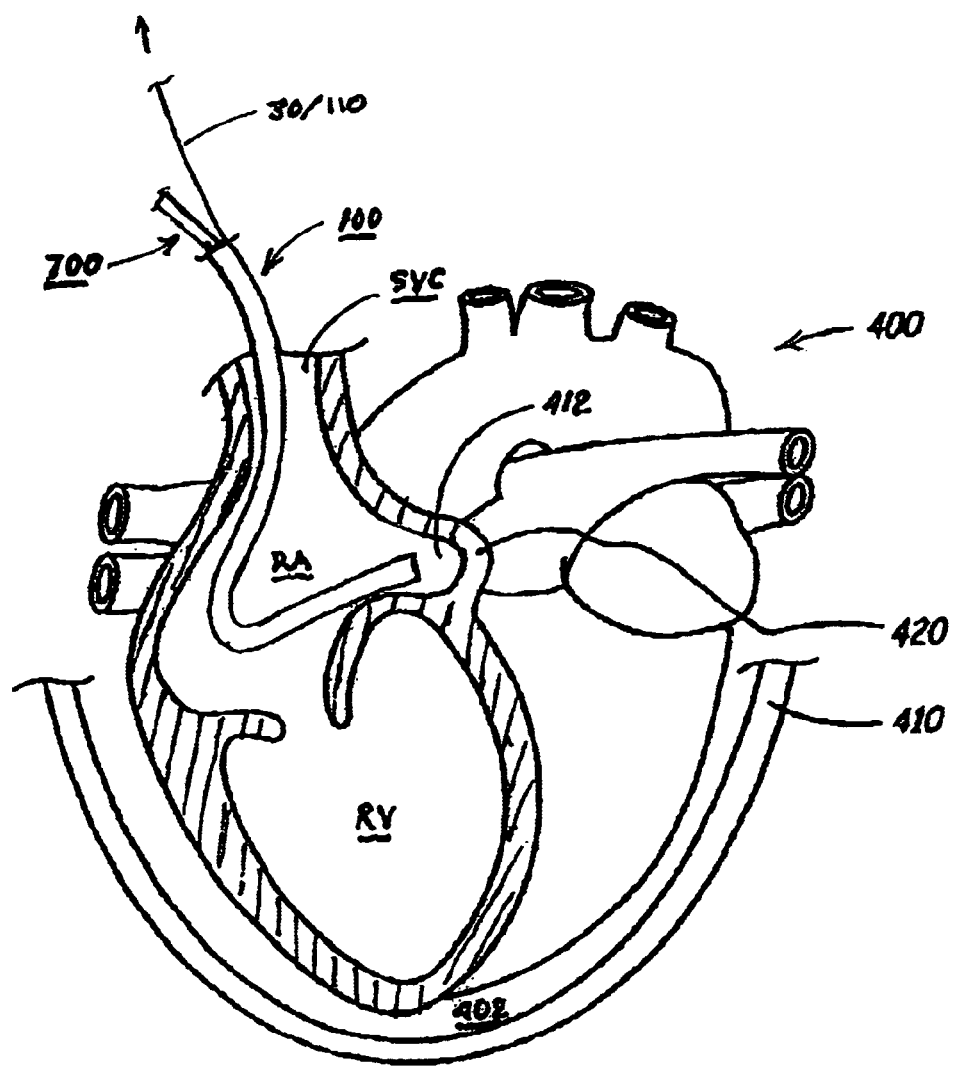
FIG. 11 is a schematic illustration of the advancement of the steerable guide catheter of FIG. 3 into the right atrium through the superior vena cava and the deflection of the guide catheter distal end into the atrial appendage.

In FIG. 11, the steerable guide catheter body 40 of FIG. 3 is advanced into the RA through the SVC, and the guide catheter distal end 16 is directed toward the right atrial wall 420 by selectively operating the deflection wire 30/110 to induce a bend in segment 52 as shown in FIG. 1. The fixation catheter 700 is advanced through the guide catheter delivery lumen to dispose the distal fixation helix 746 toward the right atrial wall 420.

Figure 12:
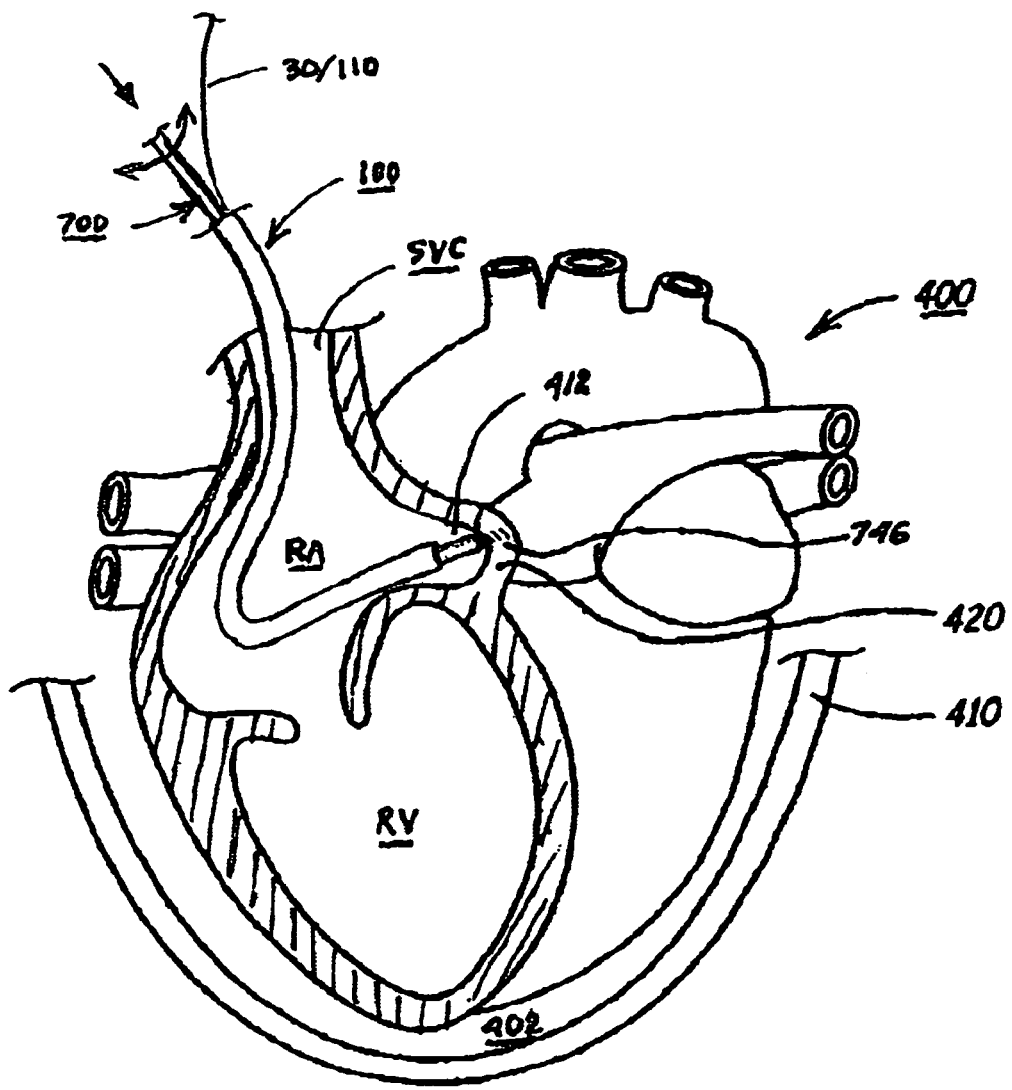
FIG. 12 is a schematic illustration of the advancement of the distal segment of the fixation catheter of FIG. 5 out of the guide catheter delivery lumen and the rotation of the fixation helix into the atrial wall.
Figure 13:
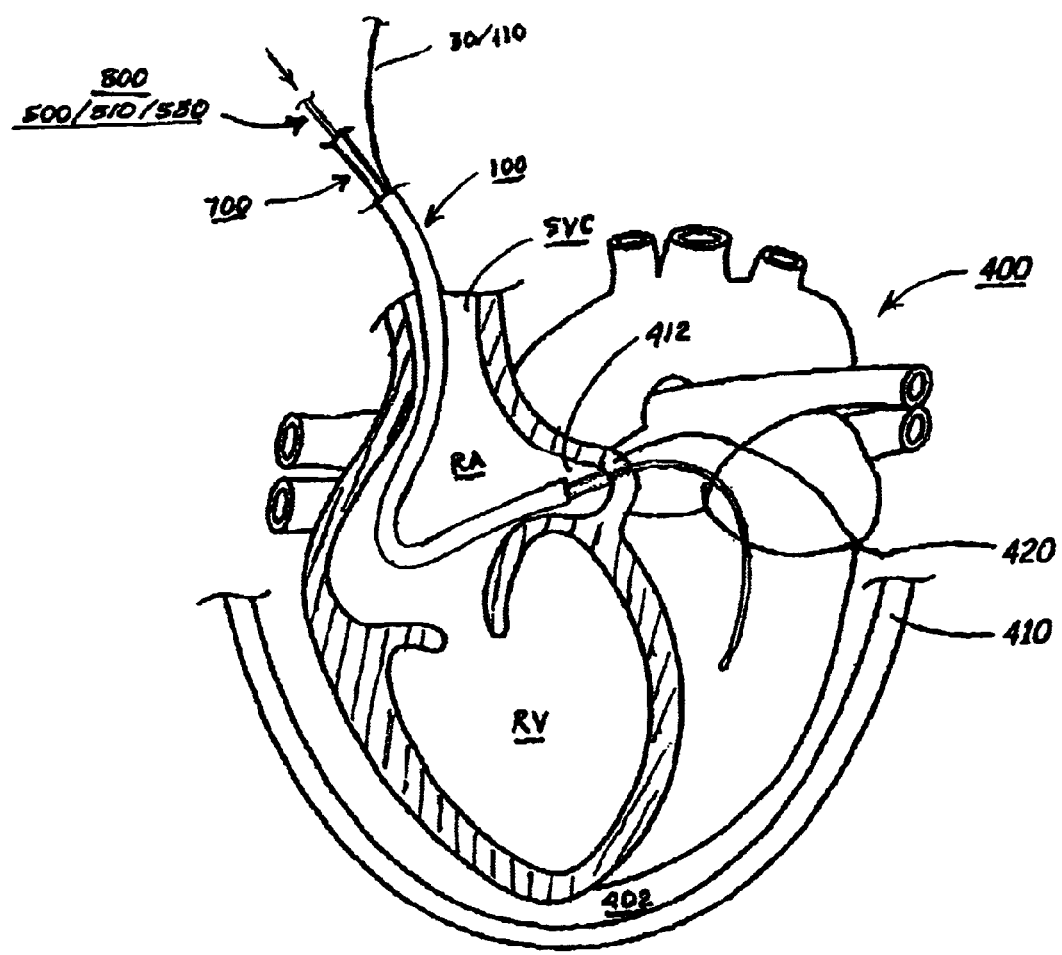
FIG. 13 is a schematic illustration of the advancement of one of a tissue penetration instrument, a therapeutic catheter, and an electrical medical lead through the fixation catheter lumen, the distal seal, the atrial wall and into the pericardial space.

As shown in FIG. 12, the distal segment of the fixation catheter 700 is extended out of the guide catheter delivery lumen, and the fixation helix 746 is rotated to screw it into the atrial wall 420 as shown in greater detail in FIG. 6. In FIG. 13, one of a tissue penetration instrument 800, a therapeutic catheter 500, and an electrical medical lead 510/530 are extended through the fixation catheter lumen, the distal seal, the atrial wall, and into the pericardial space 402 in the manner shown in detail in FIG. 7.

The tissue penetration instrument 800 can be removed if it is not necessary to employ it in the advancement of a distal segment of the therapeutic catheter 500 or the electrical medical lead 510/530 into the pericardial space 402. If the tissue penetration instrument 800 is employed, and if it is or functions as a guidewire, then it is left in place so that the one of the therapeutic catheter 500 or the electrical medical lead 510/530 can be advanced over it. Then, the penetration instrument 800 is retracted leaving the distal segment of one of the therapeutic catheter 500 or the electrical medical lead 510/530 within the pericardial space 402.

The steerable guide catheter 100 is removed either before or after the advancement of a distal segment of the therapeutic catheter 500 or the electrical medical lead 510/530 into the pericardial space 402 by retracting it over the fixation catheter 700. The steerable guide catheter 100 is retracted and removed from over the fixation catheter 700, leaving it in place with the fixation helix 746 screwed into the right atrial wall 420 as shown in FIG. 13.

Figure 14:
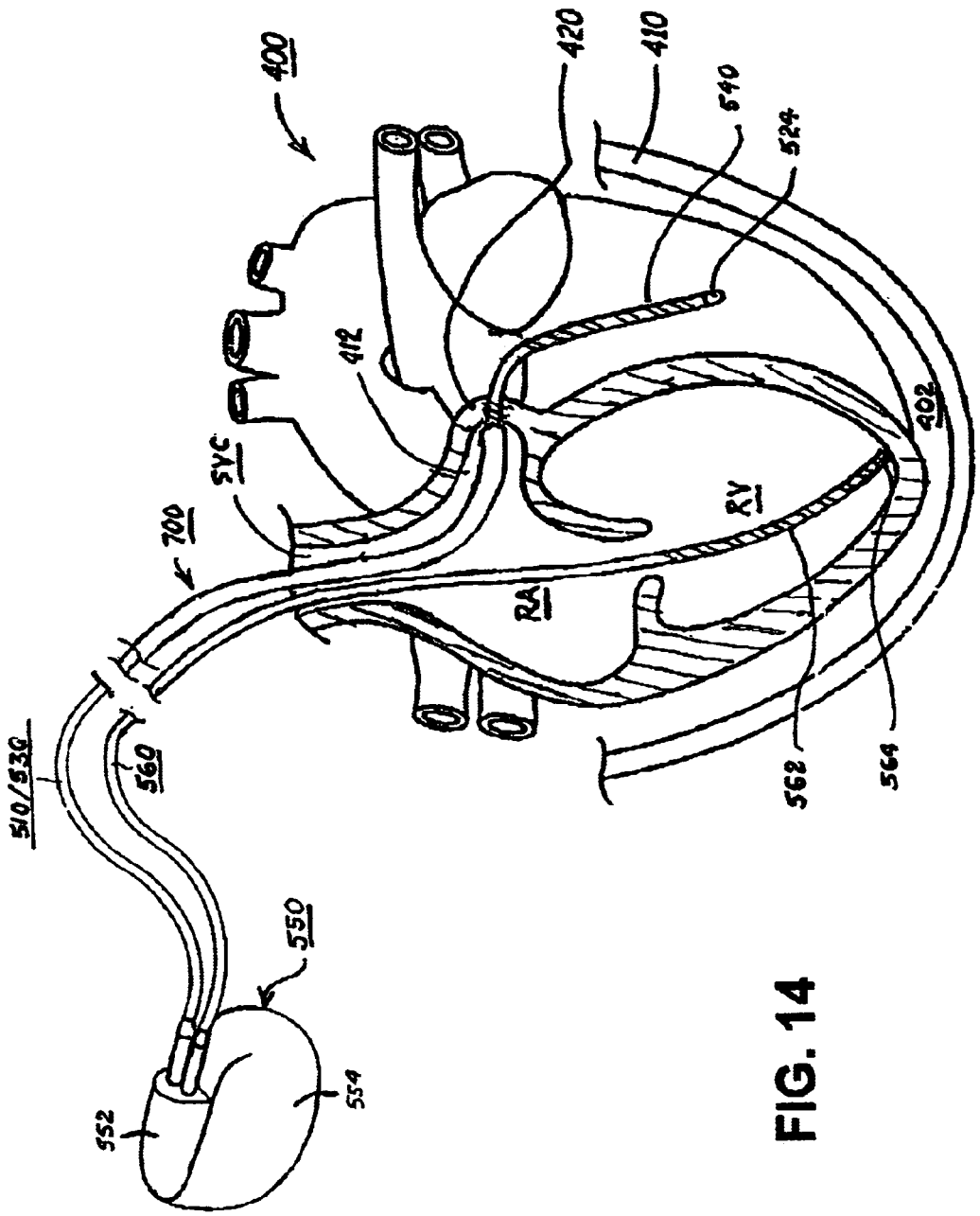
FIG. 14 is a schematic illustration of the coupling of the proximal ends of a pair of cardioversion/defibrillation leads incorporating electrodes of FIGS. 9 and 10 with an ICD IPG following removal of the steerable guide catheter enabling implantation of the ICD IPG subcutaneously in the thoracic region.

FIG. 14 is a schematic illustration of the coupling of the proximal end of an electrical medical lead 510 of FIG. 9 or 530 of FIG. 10 with a implantable cardioverter/defibrillator (ICD) IPG 550 following removal of the steerable guide catheter 100 enabling implantation of the IPG 550 subcutaneously in the thoracic region. The depicted electrical medical lead 510/530 incorporates both an elongated cardioversion/defibrillation electrode 540 and a distal tip pace/sense electrode 524. The cardioversion/defibrillation electrode 540 and a distal tip pace/sense electrode 524 are advanced through the lumen and penetrable seal of the fixation catheter 700 and through the atrial wall 420 and disposed in the pericardial space 402 in the manner described above. The ICD IPG 550 is also coupled to a second electrical medical lead 560 that is transvenously advanced through the SVC and RA to dispose an elongated cardioversion/defibrillation electrode 562 and a distal tip pace/sense electrode 564 in the RV.

The ICD IPG 550 comprises a hermetically sealed enclosure or housing 554 that encloses electrical circuitry and a battery power source and a connector header 552 having connector bores that the lead connector assemblies fit into to couple the lead electrodes to the electrical circuitry in a manner well known in the art. The electrical circuitry may be coupled to the exterior electrically conductive surface of the housing 554 to form an indifferent electrode for pacing and/or cardioversion/defibrillation. The ICD IPG may comprise the MEDTRONIC® Marquis® VR or DR ICD IPG, for example, that senses electrical heart activity and delivers pacing pulses between the pace/sense electrodes 524 and 564 and delivers cardioversion/defibrillation shocks between the elongated cardioversion/defibrillation electrodes 540 and 562 in response to detection of a ventricular tachycardias. The ICD IPG 550 may further comprise the MEDTRONIC® InSync ICD® Cardiac Resynchronization and ICD System IPG that delivers synchronized pacing pulses to the right and left ventricles through the pace/sense electrodes 564 and 524, respectively.

It will be understood that a bi-ventricular pacemaker IPG may be substituted for the ICD IPG 550 and employed with pacing leads 510 of FIG. 9 with pace/sense electrodes 522 and 524 disposed in pericardial space 402 and one of the RA and RV to provide multi-chamber pacing therapies. It will also be understood that the implantable medical lead 510/530 may further support a physiologic sensor 520 that is coupled with circuitry within the ICD IPG 550 or a multi-chamber pacemaker IPG and employed in the determination of a pacing rate or the detection of a tachyarrhythmia.

Figure 15:
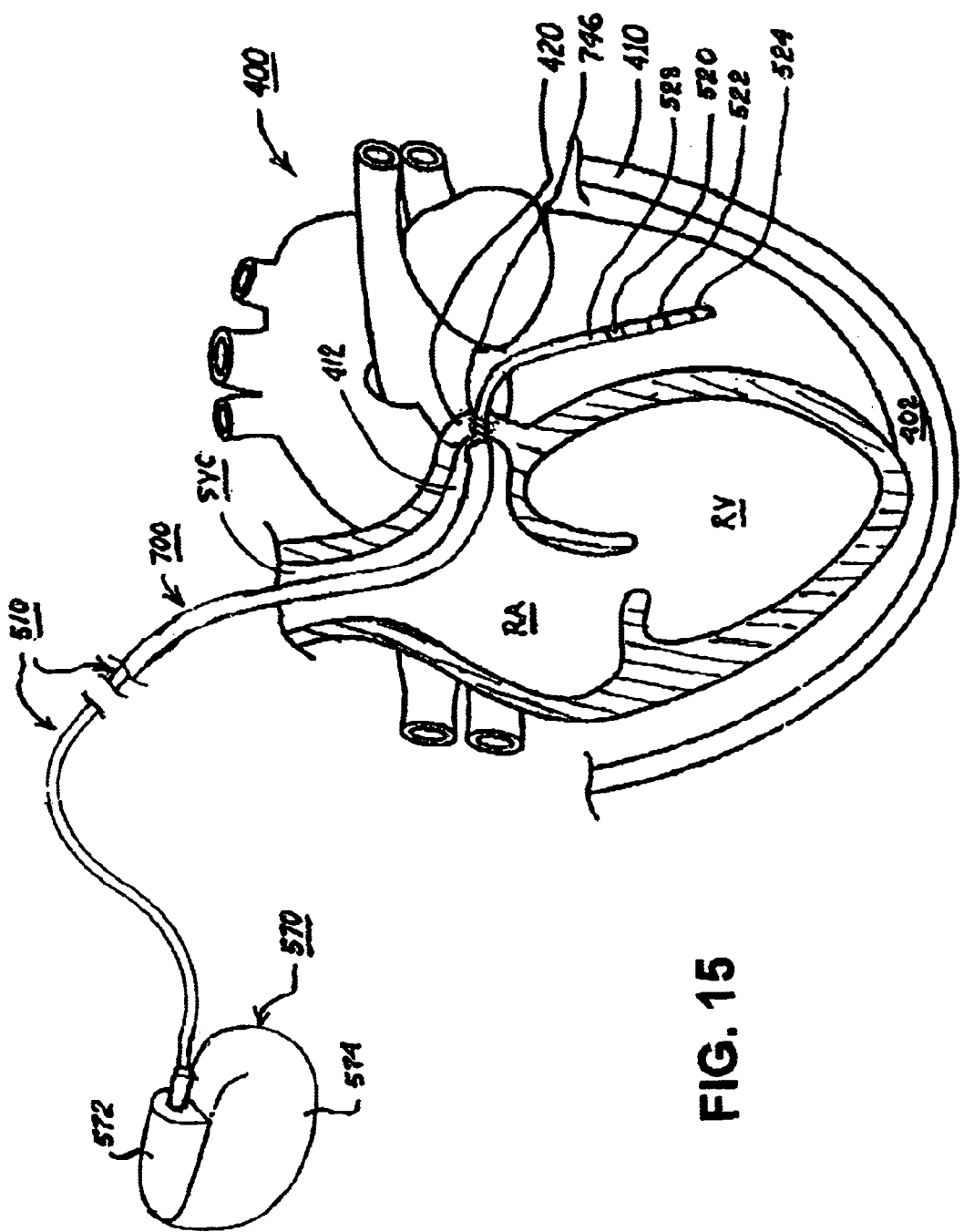
FIG. 15 is a schematic illustration of the coupling of the proximal end of an electrical medical lead of FIG. 9 or FIG. 10 with an IPG following removal of the steerable guide catheter enabling implantation of the IPG subcutaneously in the thoracic region.

Elaborate implantable hemodynamic monitors (IHMs) for recording the EGM from electrodes placed in or about the heart and other physiologic sensor derived signals, e.g., one or more of blood pressure, blood gases, temperature, electrical impedance of the heart and/or chest, and patient activity have been proposed in the prior art. FIG. 15 is a schematic illustration of the coupling of the proximal end of an electrical medical lead 510 of FIG. 9 with an IHM 570 following removal of the steerable guide catheter 100 enabling implantation of the IHM 570 subcutaneously in the thoracic region. The depicted electrical medical lead 510 supports the physiologic sensor 520 and/or one or both of the sense electrodes 522 and 524 on the lead body 528 disposed in the pericardial space 402. The physiologic sensor 520 and/or one or both of the sense electrodes 522 and 524 are advanced through the lumen and penetrable seal of the fixation catheter 700 and through the atrial wall 420 and disposed in the pericardial space 402 in the manner described above. The IHM 570 comprises a hermetically sealed enclosure or housing 574 that encloses electrical circuitry and a battery power source and a connector header 572 having connector bores that the lead connector assemblies fit into to couple the lead electrodes and sensor 520 to the electrical circuitry in a manner well known in the art. The electrical circuitry may be coupled to the exterior electrically conductive surface of the housing 554 to form an indifferent electrode for far field EGM sensing.

Figure 16:
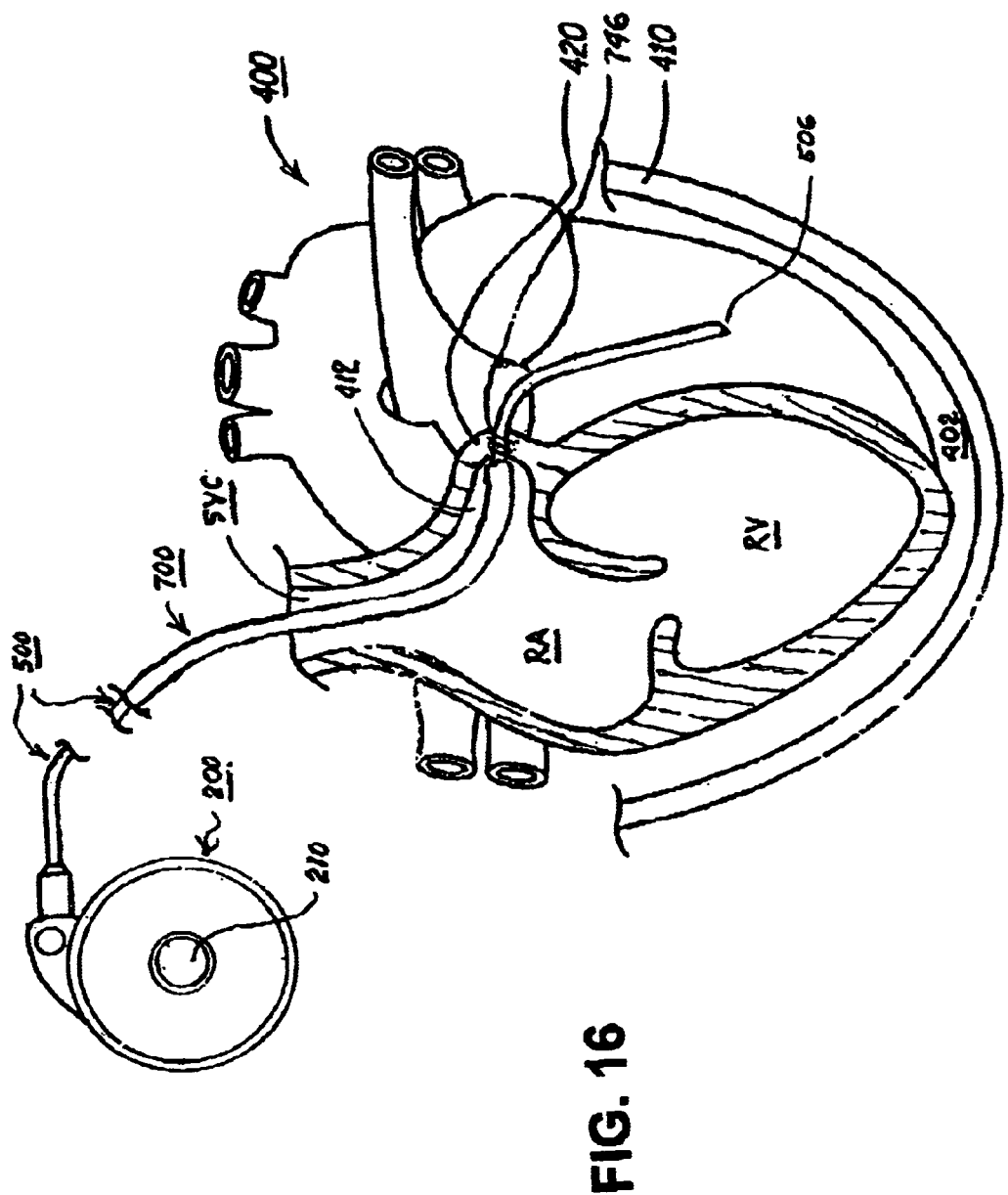
FIG. 16 is a schematic illustration of the coupling of the proximal end of a drug infusion therapeutic catheter of FIG. 8 with an implantable drug dispenser following removal of the steerable guide catheter enabling implantation of the implantable drug dispenser subcutaneously in the thoracic region.

FIG. 16 is a schematic illustration of the coupling of the proximal end of a drug infusion catheter 500 of FIG. 8 with an implantable drug dispenser following removal of the steerable guide catheter 100 enabling implantation of the implantable drug dispenser subcutaneously in the thoracic region. The therapeutic catheter 500 is depicted in FIG. 14 extending between such an IIP 200 implanted subcutaneously in the thoracic region of the body through a venous pathway and through the superior vena cava SVC into the RA and through the right atrial wall 420 into the pericardial space 402. The IIP 200 is coupled to the proximal end of the drug delivery catheter 500 and implanted subcutaneously in a thoracic region of the patient's body. The IIP 200 and therapeutic catheter 500 may take the form of the Medtronic® SynchroMed® Infusion System. The battery powered IIP 200 can be advantageously programmed to frequently or continuously deliver drug boluses of drugs that have a short duration of activity directly to an efficacious site. The IIP 200 is surgically implanted subcutaneously under the skin such that the refill port 210 is directed outward. The IIP reservoir can be refilled through port 210 accessed transcutaneously as necessary. Adverse side effects are reduced and the mental and physical states of many patients are improved by the automatically administered drug therapy. It is not necessary to rely upon the patient to comply with the prescribed regimen.

It will be understood that structure and functions of both the IIP 200 and an IPG or IHM of the types described in reference to FIGS. 14-16 may be combined into a single implantable medical device.

A variety of deflectable or steerable stylets and guidewires have been proposed, and in some cases clinically introduced, to aid in direct implantation of an endocardial cardiac lead having a lead body lumen. One approach has been to employ deflectable stylets wherein the stylet distal segment can be deflected or curved while within the lead body lumen from the proximal end thereof. Thus, it is conceived that such steerable stylets or guidewires can be employed instead of the steerable guide catheter 100 to advance the fixation catheter 700 through the venous pathway, the SVC the RA and into the atrial appendage and to deflect the fixation catheter distal end and fixation helix 746 toward the atrial wall 420 in the atrial appendage 412.

Figure 17:
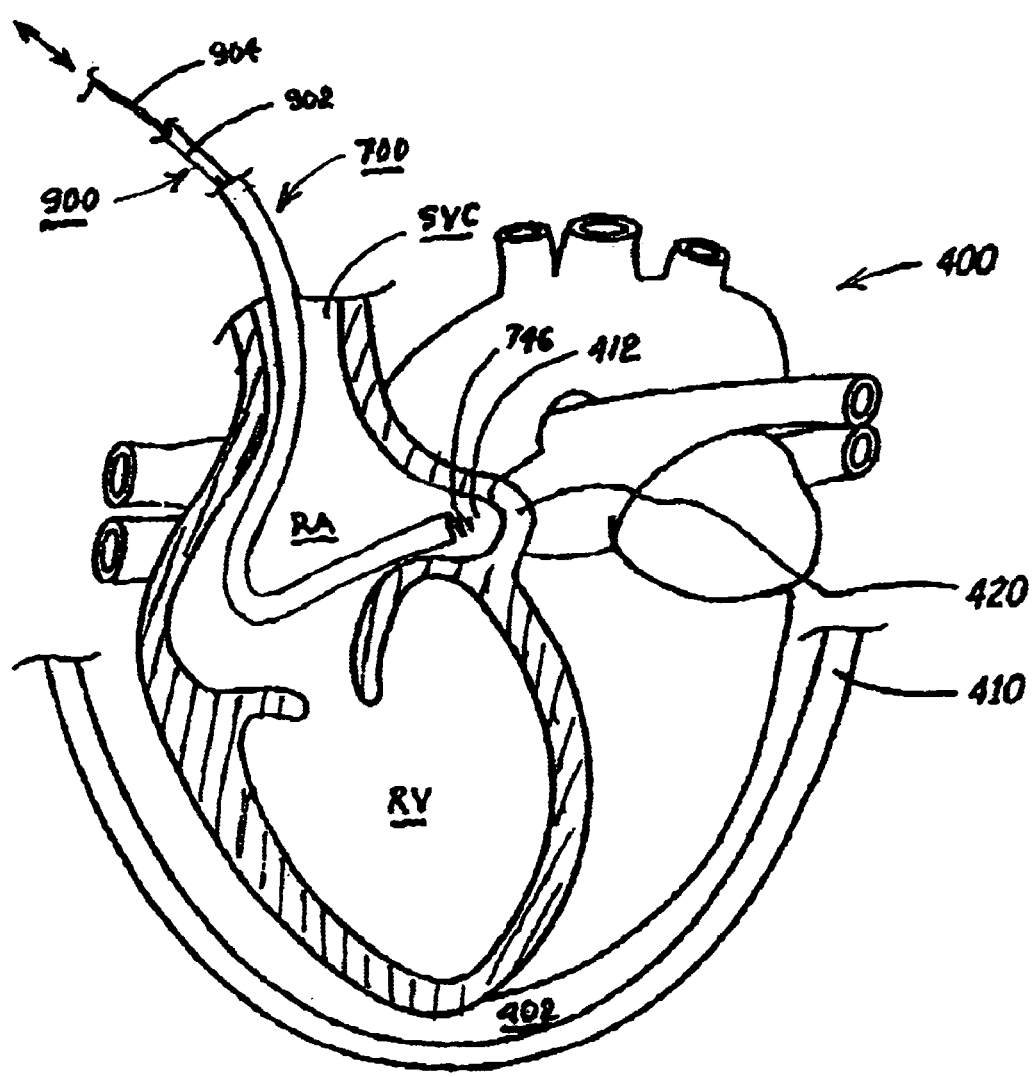
FIG. 17 is a schematic illustration of the advancement of the fixation catheter of FIG. 5 into the right atrium through the superior vena cava and the deflection of the fixation probe distal end into the atrial appendage employing a steerable stylet or guidewire.

Use of a two-piece steerable stylet (or guidewire) 900 to accomplish the advancement and to deflect the fixation catheter distal end and fixation helix 746 toward the atrial wall 420 is depicted in FIG. 17. The two-piece steerable stylet 900 comprises a straight, tubular, outer sleeve or member 902 and a curved inner wire 904 or member received within the outer member lumen enabling relative movement of the inner and outer members as disclosed in U.S. Pat. No. 5,728,148 to Bostrom et al, for example. The outer member of the '148 patent is relatively straight when unrestrained, and a curve can be induced in the inner member. The curvature of the inner member 904 induces a like curvature in the outer member 902 when the inner member 904 is advanced distally through the lumen of the outer member 902. Alternatively, a two-piece stylet 900 comprising a curved outer member 902 and a relatively straight inner member 904 are also known to the art. In such a two-piece stylet 900, the relative position of the inner member 904 with respect to the outer member 902 determines the degree to which the curved member (inner or outer) is allowed to display its preset curvature. The inner member 904 can be completely withdrawn from the lumen of the outer member 902 in such a two-piece steerable stylet 900.

Further steerable stylets (or guidewires) have been developed or proposed where the inner member distal end is attached to the outer member 902 at or near the outer member distal end, and the outer member 902 is fabricated to enable selective deflection of a distal segment thereof. Such a steerable stylet 900 typically employs an outer member 902 that is generally straight when unrestrained and the inner member 904 functions as a deflection wire (also referred to as a traction wire, a pull wire, a push wire or a push-pull wire) extending through a lumen of the outer member to an attachment point at or near the outer member distal end. The inner member 904 or deflection wire is pushed or pulled on at its proximal end typically through a handle that is permanently or removably attached to the outer member proximal end. The proximal retraction or distal advancement of the inner member 904 or deflection wire causes at least a distal segment of the outer member 902 to bend or deflect. An example of such a deflection mechanism can be found in U.S. Pat. Nos. 4,815,478, and 6,146,338, for example, which disclose the use of a push-pull wire extending through a guidewire lumen for deflecting a guidewire distal end by manipulating the push-pull wire at the guidewire proximal end. The '338 patent discloses a steerable stylet handle at the stylet body proximal end that is manipulated by one hand operation to induce a bend in a distal segment of the stylet outer member 902.

In FIG. 17, the curvature of the steerable stylet outer member 902 of either of the above-described types induces a like curvature in the fixation catheter 700 that deflects the distal fixation helix 746 into the atrial appendage 412 and toward the atrial wall 420. The implanting physician can rotate the fixation catheter proximal end to screw the fixation helix 746 into the right atrial wall 420 as described above.

Typically, such a two-piece steerable stylet 900 does not have an enlarged proximal handle or end or the handle can be removed, and other instruments having through lumens can be advanced over the outer member 902 or the inner member 904 if the outer member can be removed. Advantageously, referring again to FIG. 7, the inner member 904 or the outer member 902 (or both) may function as a penetration instrument 800 that is advanced more distally within the turns of the fixation helix 746 through the atrial wall 420. The inner member 904 or outer member 902 (or both) may function as a guidewire enabling advancement of a further electrical medical lead 500/510 or catheter 530 over the stylet/guidewire 900 to dispose the distal segment thereof in the pericardial space 402.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice.

It is to be understood, that within the scope of the appended claims, the invention may be practiced otherwise than as specifically described without actually departing from the spirit and scope of the present invention. The disclosed embodiments are presented for purposes of illustration and not limitation, and the present invention is limited only by the claims that follow.

What is claimed is:

1. A system for accessing a desired location through a tissue wall within a patient's body; comprising:

an elongated fixation catheter having a fixation catheter lumen extending between proximal and distal fixation catheter lumen openings, a penetrable seal closing the distal fixation catheter lumen opening, and a distal tissue fixation mechanism, an elongated steerable fixation instrument adapted to engage the elongated fixation catheter and steer the guide catheter distal end to the tissue wall, the steerable fixation instrument enabling extension of the distal fixation mechanism into the tissue wall to engage and stabilize the tissue wall;

an elongated penetration instrument comprising a guidewire having a tissue penetrating distal tip sized and adapted to be passed through the fixation catheter lumen, through the penetrable seal, and through the tissue wall, thereby creating a perforation through the tissue wall and into the desired location; and a therapeutic catheter having a therapeutic catheter lumen terminating in at least one distal therapeutic catheter lumen opening adapted to be advanced over the guidewire and through the fixation catheter lumen, through the penetrable seal, and through the tissue wall perforation to dispose the distal therapeutic catheter lumen opening in the desired location.

2. The system of claim 1, wherein the therapeutic catheter comprises one of a therapeutic agent delivery catheter, a gene delivery catheter, a fluid sampling catheter and a drainage catheter.

3. The system of claim 1, wherein the therapeutic catheter comprises one of a therapeutic agent delivery catheter, a gene delivery catheter, a fluid sampling catheter and a drainage catheter.

4. The system of claim 1, wherein:
the steerable fixation instrument further comprises a steerable guide catheter having a guide catheter delivery lumen terminating in a delivery lumen exit port at a guide catheter distal end, a deflectable distal segment, and a deflector operable from the guide catheter proximal end to steer the guide catheter distal end to the tissue wall; and
the fixation catheter sized to be extend through said guide catheter delivery lumen to dispose said distal fixation mechanism and distal fixation catheter lumen opening proximate the tissue wall, the elongated fixation catheter adapted to be manipulated to extend the distal fixation mechanism away from the distal guide catheter delivery lumen opening into the tissue wall to engage and stabilize the tissue wall.

5. The system of claim 4, wherein the steerable guide catheter further comprises a guide catheter hub and an elongated guide catheter body having a guide catheter body sidewall extending between a guide catheter body proximal end and a guide catheter body distal end, the guide catheter body further comprising:
a delivery lumen extending between a delivery lumen entry port and a delivery lumen exit port at the guide catheter body distal end;
a deflection wire lumen extending between a wire port through the sidewall of the guide catheter body and a deflection wire lumen distal end; and
a deflection wire extending from a deflection wire proximal end through the wire port and through the deflection wire lumen to a deflection wire distal end fixed to the guide catheter body at the deflection wire lumen distal end.

6. The system of claim 1, wherein the steerable fixation instrument further comprises a steerable stylet having a tubular outer member having an outer member lumen and an inner member disposed in the outer member lumen, the tubular outer member sized to extend through the fixation catheter lumen, and the outer and inner members selectively movable with respect to one another to deflect a distal segment of the outer member and to thereby deflect a distal segment of the fixation catheter and to steer the fixation catheter distal end to the tissue wall.

7. The system of claim 6, wherein the steerable stylet functions as the elongated penetration instrument having a tissue-penetrating element sized and adapted to be passed through the fixation catheter lumen, through the penetrable seal, and through the tissue wall, thereby creating a perforation through the tissue wall and into the desired location.

8. The system of claim 6, wherein at least one of the inner and outer tubular members is extendable through the fixation catheter lumen, through the penetrable seal, and through the tissue wall and into the desired location.

9. The system of claim 1, wherein the distal tissue fixation mechanism comprises a distal tissue fixation helix, and the elongated fixation catheter is adapted to be rotated to screw the distal fixation helix into the tissue wall to engage and stabilize the tissue wall.

10. The system of claim 9, wherein the steerable fixation instrument further comprises a steerable stylet having a tubular outer member having an outer member lumen and an inner member disposed in the outer member lumen, the tubular outer member sized to extend through the fixation catheter lumen, and the outer and inner members selectively movable with respect to one another to deflect a distal segment of the outer member and to thereby deflect a distal segment of the fixation catheter and to steer the fixation helix toward the tissue wall.

11. The system of claim 10, wherein the steerable stylet functions as the elongated penetration instrument having a tissue-penetrating element sized and adapted to be passed through the fixation catheter lumen, through the penetrable seal, and through the tissue wall, thereby creating a perforation through the tissue wall and into the desired location.

12. The system of claim 9, wherein:
the steerable fixation instrument further comprises a steerable guide catheter having a guide catheter delivery lumen terminating in a delivery lumen exit port at a guide catheter distal end, a deflectable distal segment, and a deflector operable from the guide catheter proximal end to steer the guide catheter distal end to the tissue wall; and
the fixation catheter sized to be extend through said guide catheter delivery lumen to dispose said distal fixation helix and distal fixation catheter lumen opening proximate the tissue wall, the elongated fixation catheter adapted to be manipulated to extend the distal fixation helix away from the distal guide catheter delivery lumen opening to the tissue wall to enable screwing the fixation helix into the tissue wall.

13. The system of claim 9, wherein the elongated penetration instrument comprises one of a guidewire or a stylet having a tissue penetrating distal tip.

14. The system of claim 9, further comprising a therapeutic catheter having a therapeutic catheter lumen terminating in at least one distal therapeutic catheter lumen opening adapted to be advanced through the fixation catheter lumen, through the penetrable seal, and through the tissue wall perforation to dispose the distal therapeutic catheter lumen opening in the desired location.

15. The system of claim 14, wherein the therapeutic catheter comprises one of a therapeutic agent delivery catheter, a gene delivery catheter, a fluid sampling catheter and a drainage catheter.

16. The system of claim 9, wherein:
the elongated penetration instrument comprises a guidewire having a tissue penetrating distal tip; and
a therapeutic catheter having a therapeutic catheter lumen terminating in at least one distal therapeutic catheter lumen opening adapted to be advanced over the guidewire through the fixation catheter lumen, through the penetrable seal, and through the tissue wall perforation to dispose the distal therapeutic catheter lumen opening in the desired location.

17. The system of claim 16, wherein the therapeutic catheter comprises one of a therapeutic agent delivery catheter, a gene delivery catheter, a fluid sampling catheter, and a drainage catheter.

18. The system of claim 9, wherein the elongated penetration instrument comprises a therapeutic catheter having a tissue penetrating distal tip and a therapeutic catheter lumen terminating in at least one distal therapeutic catheter lumen opening adapted to be advanced through the fixation catheter lumen, through the penetrable seal, and through the tissue wall to dispose the distal therapeutic catheter lumen opening in the desired location.

19. The system of claim 18, wherein the therapeutic catheter comprises one of a therapeutic agent delivery catheter, a gene delivery catheter, a fluid sampling catheter, and a drainage catheter.

20. A system for accessing a desired location through a tissue wall within a patient's body; comprising:
    an elongated fixation catheter having a fixation catheter lumen extending between proximal and distal fixation catheter lumen openings, a penetrable seal closing the distal fixation catheter lumen opening, and a distal tissue fixation mechanism,
    an elongated steerable fixation instrument comprising a steerable guide catheter that comprises a guide catheter hub and an elongated guide catheter body having a guide catheter body sidewall extending between a guide catheter body proximal end and a guide catheter body distal end, the guide catheter body further comprising:
    a delivery lumen extending between a delivery lumen entry port and a delivery lumen exit port at the guide catheter body distal end;
    a deflection wire lumen extending between a wire port through the sidewall of the guide catheter body and a deflection wire lumen distal end; and
    a deflection wire extending from a deflection wire proximal end through the wire port and through the deflection wire lumen to a deflection wire distal end fixed to the guide catheter body at the deflection wire lumen distal end; and
    an elongated penetration instrument having a tissue-penetrating element sized and adapted to be passed through the fixation catheter lumen, through the penetrable seal, and through the tissue wall, thereby creating a perforation through the tissue wall and into the desired location,
    wherein the fixation catheter is sized to be extend through said guide catheter delivery lumen to dispose said distal fixation mechanism and distal fixation catheter lumen opening proximate the tissue wall, the elongated fixation catheter adapted to be manipulated to extend the distal fixation mechanism away from the distal guide catheter delivery lumen opening into the tissue wall to engage and stabilize the tissue wall.

21. A system for accessing a desired location through a tissue wall within a patient's body; comprising:
    an elongated fixation catheter having a fixation catheter lumen extending between proximal and distal fixation catheter lumen openings, a penetrable seal closing the distal fixation catheter lumen opening, and a distal tissue fixation mechanism,
    an elongated steerable fixation instrument comprising a steerable stylet having a tubular outer member having an outer member lumen and an inner member disposed in the outer member lumen, the tubular outer member sized to extend through the fixation catheter lumen, and the outer and inner members selectively movable with respect to one another to deflect a distal segment of the outer member and to thereby deflect a distal segment of the fixation catheter and to steer the fixation catheter distal end to the tissue wall and adapted to engage the elongated fixation catheter and steer the guide catheter distal end to the tissue wall, the steerable fixation instrument enabling extension of the distal fixation mechanism into the tissue wall to engage and stabilize the tissue wall; and
    an elongated penetration instrument having a tissue-penetrating element sized and adapted to be passed through the fixation catheter lumen, through the penetrable seal, and through the tissue wall, thereby creating a perforation through the tissue wall and into the desired location.

* * * * *